(12) United States Patent
Bhushan et al.

(10) Patent No.: US 8,858,913 B2
(45) Date of Patent: Oct. 14, 2014

(54) MULTIMERIC PEPTIDOMIMETIC FIBROSIS SPECIFIC DUAL-MODALITY PROBES

(75) Inventors: Kumar Ranjan Bhushan, St Louis, MO (US); Preeti Misra, St Louis, MO (US)

(73) Assignee: Preeti Misra

( * ) Notice: Subject to any disclaimer, the term of this patent is extended or adjusted under 35 U.S.C. 154(b) by 71 days.

(21) Appl. No.: 13/595,515

(22) Filed: Aug. 27, 2012

(65) Prior Publication Data

US 2014/0058072 A1    Feb. 27, 2014

(51) Int. Cl.
*A61K 49/00* (2006.01)
*A61K 49/10* (2006.01)
*A61B 5/00* (2006.01)
*A61B 8/00* (2006.01)
*A61B 10/00* (2006.01)

(52) U.S. Cl.
CPC ............. *A61K 49/003* (2013.01); *A61K 49/106* (2013.01); *A61K 49/108* (2013.01)
USPC ........................................... 424/9.1; 424/9.6

(58) Field of Classification Search
CPC   A61K 49/0032;  A61K 49/106;  A61K 49/108
USPC .......................................................... 424/9.1
See application file for complete search history.

*Primary Examiner* — Michael G Hartley
*Assistant Examiner* — Melissa Perreira (57) ABSTRACT

The present invention describes dual-modality probes. In particular, the present invention discloses fibrosis specific multimeric small-molecule peptidomimetic dual-modality MRI and optical probes.

18 Claims, 7 Drawing Sheets

MULTIMERIC PEPTIDOMIMETIC FIBROSIS SPECIFIC DUAL-MODALITY PROBES

FIELD OF THE INVENTION

The present invention discloses fibrosis specific multimeric small-molecule peptidomimetic dual-modality MRI and optical probes.

BACKGROUND

Activated hepatic stellate cells and myofibroblasts HSC/MF play a central role in the development of chronic liver diseases {Friedman, 2008}. They deposit an excess of extracellular matrix components which leads to fibrosis and finally cirrhosis. Cirrhosis is defined as architectural distortion of the liver with severe vascular and functional abnormalities {Schuppan, 2008}.

Biopsy is considered the gold standard for diagnosis of cirrhosis. However, biopsy is not well-suited to the screening/monitoring disease because of its cost, associated morbidity, and known lack of accuracy because of sampling variation {Abraldes, 2012; Afdhal, 2004}. These limitations have spurred interest in alternate modalities for monitoring fibrosis and the patient's response to therapy.

SUMMARY

Imaging methods such as magnetic resonance and optical that could noninvasively and repeatedly measure integrin expression would be useful in characterizing tumors and in monitoring responses to therapeutic agents. In general, optical imaging methods have high sensitivity and are cost effective at the cell/tissue level. However, most optical imaging apparatus lacks the capacity of tomographic image reconstruction, and therefore 3-dimensional localization of signals in intact tissues/organs has rarely been achieved noninvasively {Li, 2004}. Magnetic resonance imaging (MRI) offers the advantages of being noninvasive, tomographic, and high resolution. However, MRI contrast dependent on endogenous differences in water content and on relaxation time in the tissue of interest. The specificity and sensitivity of MRI is enhanced by contrast agents based on paramagnetic metals such as gadolinium {Bottrill, 2006}.

The co-registration of different molecular imaging modalities provides complementary information. Thus development of multifunctional probes for concurrent imaging applications has become an attractive area. Combining the excellent 3D spatial resolution and unlimited depth penetration of MRI with very high sensitivity of near infrared (NIR) optical imaging should serve to traverse shortcomings of each technology {Massoud, 2003}. NIR tomography has shown the ability to localize changes in functional tissue parameters in vivo, and MRI has the advantage of multiplanar imaging capability which is useful in defining all the dimensions of the fibrotic plaque.

Concurrent imaging of liver fibrosis or fibrogenesis has been elusive. Integrin $\alpha_v\beta_6$ mediates attachment of activated epithelia to fibronectin, vitronectin, and tenascin {Breuss, 1995; Midwood, 2006} and activates profibrogenic cytokine TGFβ1 {Munger, 1999} implying its instrumental role in driving fibrogenesis. Integrin receptors frequently recognize a core amino acid sequence, Arg-Gly-Asp (RGD), in their target ligands. Therefore, inhibitors with the RGD sequence can inhibit one or a small subset of such RGD-dependent integrins, and are invaluable in defining their biological functions. However, peptidic inhibitors have several disadvantages as low molecular weight inhibitors, including their instability to serum degradation (which can be circumvented by use of small cyclic peptides {Kessler, 1982}, and poor pharmacokinetics. Nevertheless, non-RGD peptides have been discovered with high specificity and inhibitory activity for $\alpha_v\beta_6$ {Kloczewiak, 1984; Kraft, 1999}, and, as of yet, non-peptidic inhibitor of $\alpha_v\beta_6$ are not known for use in concurrent imaging of $\alpha_v\beta_6$ in liver fibrosis. Therefore, high affinity $\alpha_v\beta_6$-specific peptidomimetics are attractive candidates for concurrent hepatic fibrogenesis imaging because of the correlation of selective upregulation of $\alpha_v\beta_6$-integrin during fibrosis progression.

Nature often takes advantage of multimerization to decrease ligand off-rate and improve affinity of cell surface binders {Kitov, 2003; Mammen, 1998}. There is a general need to find suitable scaffolds for the assembly of multiple targeting ligands and contrast agents in hope that multimerization would improve the performance of cancer specific ligands.

Several different multivalent scaffolds have been used successfully in past particularly for applications in carbohydrate/lectin interactions {Lindhorst, 2002; Lundquist, 2002} but also for peptide/protein interactions {Wright, 2001} and in context of tumor targeting {Carlson, 2007; Thumshirn, 2003}. Among these scaffolds are small molecules with few conjugation sites (~2-10) and larger systems like dendrimers {Voegtle, 2007} and polymers {Haag, 2006}.

The present invention describes a development of multimeric $\alpha_v\beta_6$-integrin specific dual-modality MRI and optical probes. A non-peptidic inhibitor (3-(S)-3-benzyloxy-2-(5-(pyridin-2-ylamino)pentanoyl-amino)propionylamino)-3-(3,5-dichlorophenyl)propionic acid [BDP acid] {Popov, 2008} is multimerized for high affinity on $\alpha_v\beta_6$-integrin. The multimeric $\alpha_v\beta_6$-integrin specific dual-modality MRI and optical probes could theoretically bind multivalently and thus more avidly to target cell. Multifunctional probes for concurrent imaging applications could traverse shortcomings of each technology and could provide complementary information.

Figure 1:
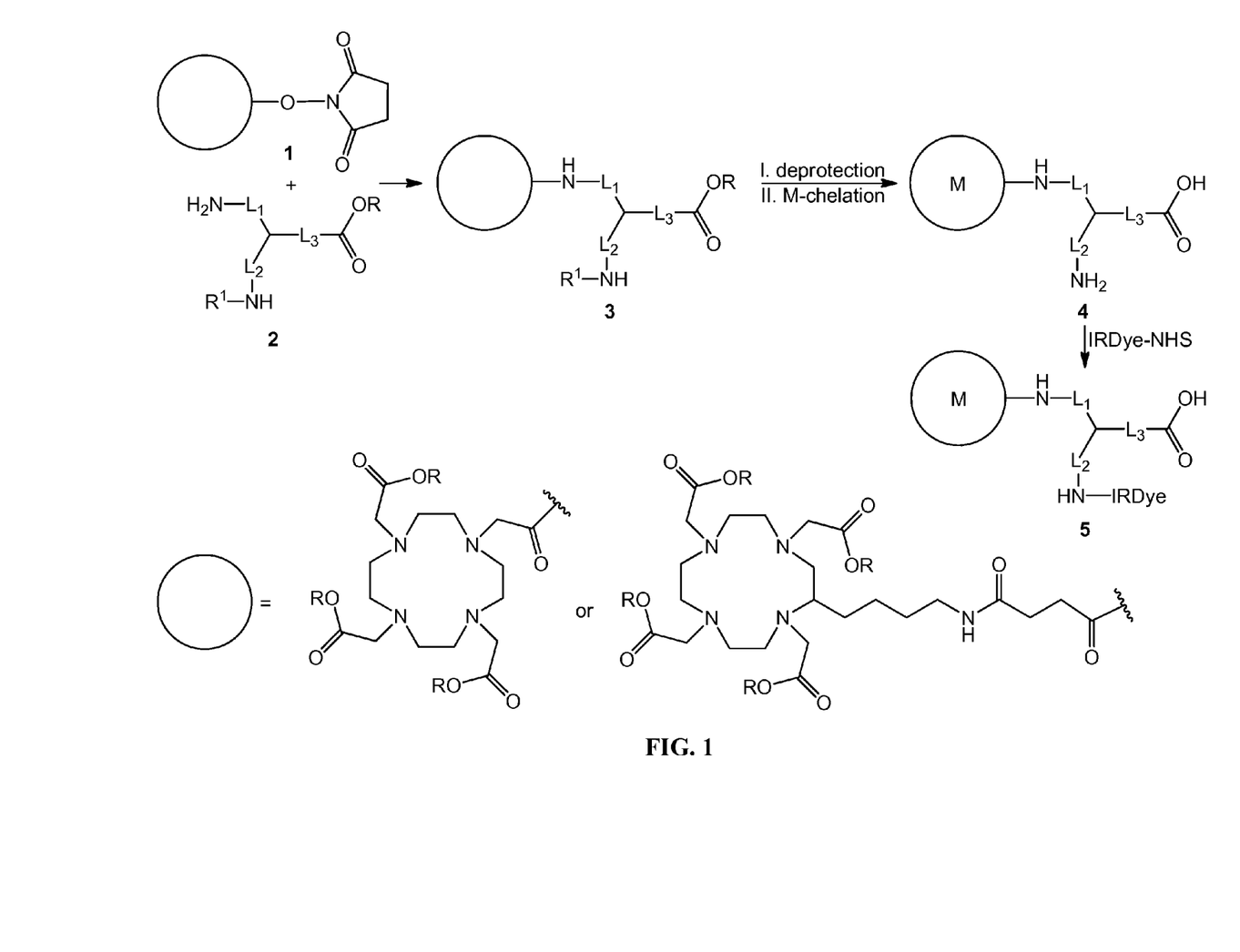
FIG. 1 represents a metal chelate and a near infrared fluorophore conjugated to a trifunctional linker moiety having carboxylic acid functional group at one end.

In one aspect of present invention, an organic chelating ligand is reacted with a trifunctional linker moiety, having primary amine and carboxylic acid functional groups, followed by deprotection of one or more functional groups to yield one or more free functional group. Chelation of a metal ion on one or more free functional group results in a metal chelate. Conjugation of a near infrared fluorophore to result in a metal chelated near infrared conjugated carboxylic acid precursor (FIG. 1). In such aspect, trifunctional linker moiety 2 is amino acid, polymer, or dendrimer. $L_1$, $L_2$ and $L_3$ are independently selected from alkane, polyethylene glycol, and polypropylene glycol. Metal ion, M is independently selected from Cu, Fe, In, Tm, Yb, Y, Gd, Eu, and a lanthanide. R is t-butyl ester, ester, or hydrogen. $R^1$ is Boc, Fmoc, Ac, Cbz, Bz, and Bn. In one embodiment, amino acid is natural amino acid. In some embodiment, amino acid is unnatural amino acid. In some embodiments, alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, IRDye is a near infrared fluorophore independently selected from the group of IRDye 800CW, IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 680.

Figure 2:
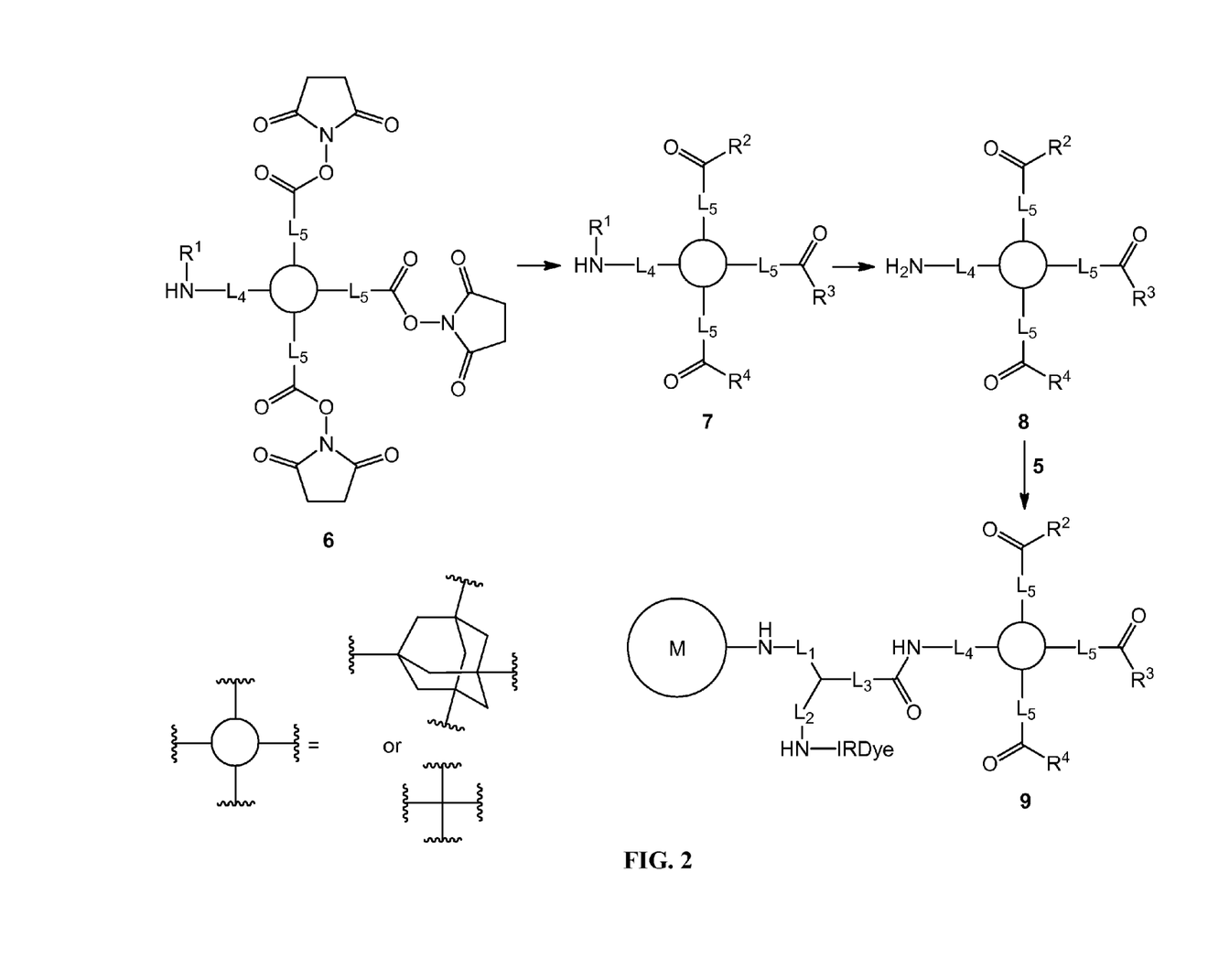
FIG. 2 represents reaction of an amine containing targeting ligand conjugated multivalent scaffold with a metal chelated near infrared conjugated carboxylic acid precursor to results in a multimeric dual-modality probe.

In an another aspect of present invention, a targeting ligand is conjugated with multivalent scaffold followed by deprotection of amino protecting group to generate an amine containing targeting ligand conjugated multivalent scaffold. Reaction of an amine containing targeting ligand conjugated multivalent scaffold with a metal chelated near infrared conjugated carboxylic acid precursor to results in multimeric dual-modality probe (FIG. 2). In such aspect, $R^1$ is independently selected from Boc, Fmoc, Ac, Cbz, Bz, and Bn. $R^2$, $R^3$ and $R^4$ are OH or $L_4$, $L_5$ and $L_6$ are linkers independently selected from alkane, amino acid, —NHCO(CH$_2$)$_5$—, polyethylene glycol, and polypropylene glycol. In one embodiment, amino acid is natural amino acid. In some embodiments, amino acid is unnatural amino acid. In some embodiments, an alkane is C0-C20 straight chain carbon unit. In some embodiments, polyethylene glycol is 1 to 20 ethylene glycol unit. In some embodiments, polypropylene glycol is 1 to 20 propylene glycol unit.

The present invention describes dual-modality probes. Particularly, the present invention discloses fibrosis specific multimeric small-molecule peptidomimetic dual-modality MRI and optical probes. Specifically, trimeric small-molecule peptidomimetic dual-modality probe have significantly higher in vitro affinity for $\alpha_v\beta_6$ in comparison to monomeric small-molecule peptidomimetic dual-modality probe.

DETAILED DESCRIPTION

In a present invention, synthetic strategy is developed for multimeric peptidomimetic dual-modality probes for targeted fibrosis imaging. Particularly, present invention describes a chemical system for the efficient production of a tri-functional agent comprised of a NIR fluorophore for optical imaging, a metal chelate for simultaneous MRI imaging, and a multimeric non-peptidic BDP acid constructed on a multivalent scaffold for targeting of $\alpha_v\beta_6$-integrin, a fibronectin/tenascin receptor, $\alpha_v\beta_3$ a promiscuous receptor for vitronectin, fibronectin, fibrinogen, and $\alpha_v\beta_5$ a vitronectin receptor.

The multimeric peptidomimetic dual-modality probes of present invention are prepared according to the methods known in the art, as illustrated in FIGS. 1-4 and described for specific compounds in examples 1-3. Products are characterized by analytical HPLC, NMR and LC-MS. Monomeric dual-modality probes are obtained in typical yields of 55-65% and trimeric dual-modality probes are obtained in typical yields of 20-30%.

FIG. 1 of present invention describes a synthetic scheme for a metal chelated near infrared conjugated carboxylic acid precursor. An organic chelating ligand is reacted with a tri-functional linker moiety, having primary amine and carboxylic acid functional groups, followed by deprotection of one or more functional groups to yield one or more free functional group. Chelation of a metal ion and conjugation of a near infrared fluorophore results in a metal chelated near infrared conjugated carboxylic acid precursor.

FIG. 2 of present invention describes a synthetic scheme for a multimeric dual-modality probe. A targeting ligand is conjugated with multivalent scaffold followed by deprotection of amino protecting group to generate an amine containing targeting ligand conjugated multivalent scaffold which react with a metal chelated near infrared conjugated carboxylic acid precursor to results in a multimeric dual-modality probe.

Figure 3:
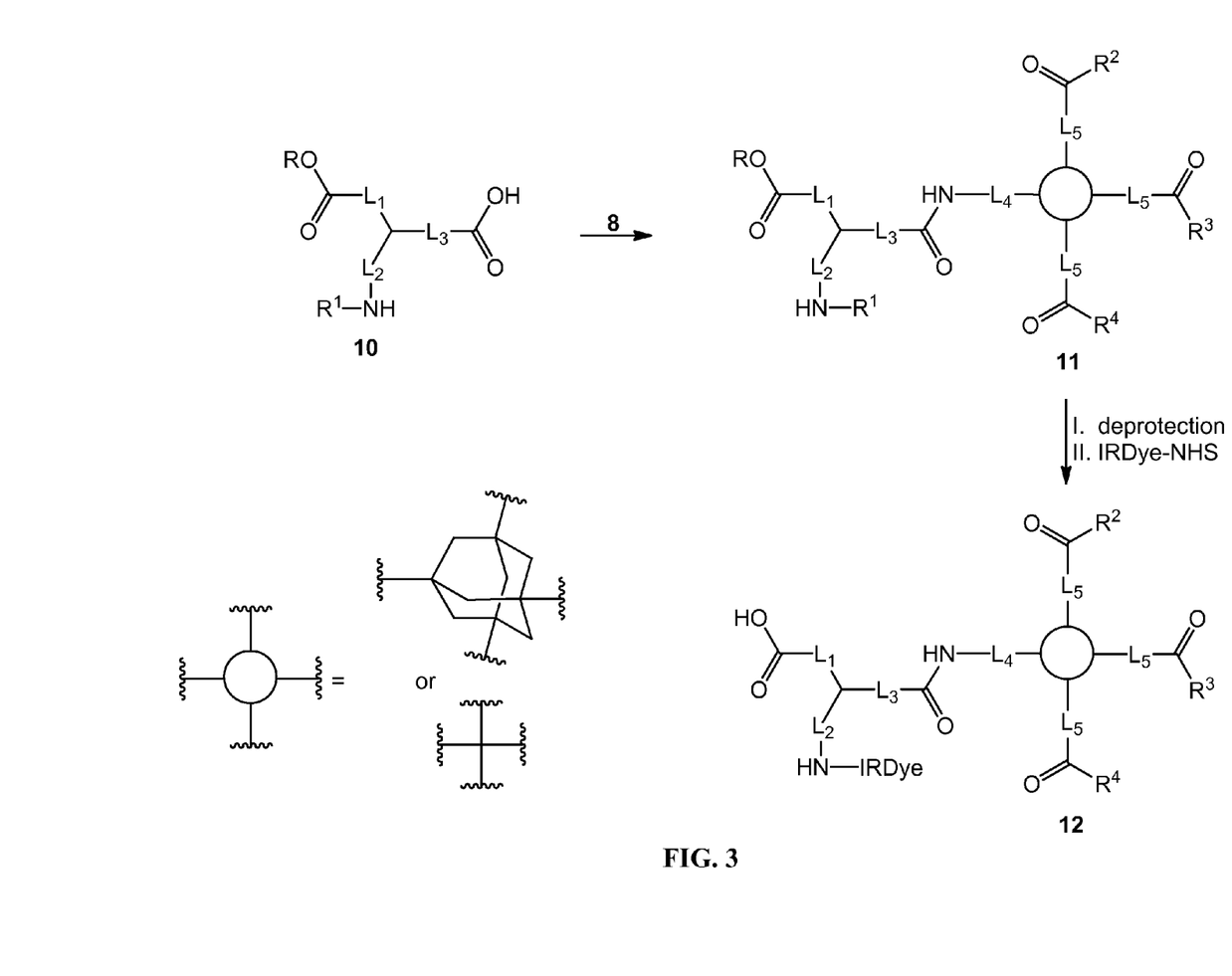
FIG. 3 represents formation of a near infrared containing targeting ligand conjugated multivalent scaffold carboxylic acid precursor.

FIG. 3 of present invention describes a synthetic scheme for a near infrared containing targeting ligand conjugated multivalent scaffold carboxylic acid precursor. An amine containing targeting ligand conjugated multivalent scaffold is reacted with a trifunctional linker moiety, followed by deprotection and conjugation with a near infrared fluorophore to results in a near infrared containing targeting ligand conjugated multivalent scaffold carboxylic acid precursor.

Figure 4:
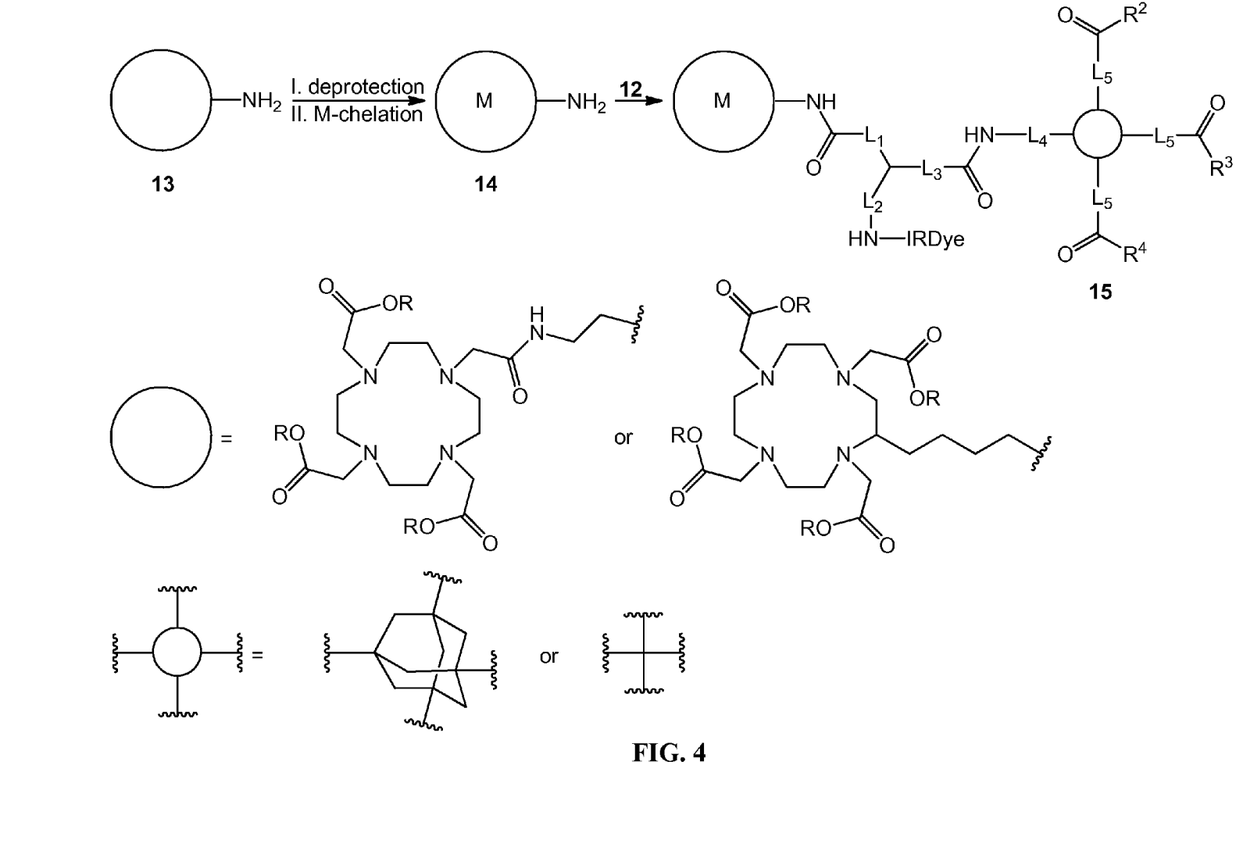
FIG. 4 represents reaction of a metal chelate with a near infrared containing targeting ligand conjugated multivalent scaffold carboxylic acid precursor to results in a multimeric dual-modality probe.

FIG. 4 of present invention describes a synthetic scheme for a multimeric dual-modality probe. Metal ion is chelated on organic chelating ligand followed by reaction with a near infrared containing targeting ligand conjugated multivalent scaffold carboxylic acid precursor to results in a multimeric dual-modality probe.

In one aspect, the present invention provides a dual-modality probe having a formula selected from the group of:

-continued

In such aspect, is  or

R is $L_1$, $L_2$, $L_3$, $L_4$, $L_5$ and $L_6$ are linkers,

IRDye is a near infrared dye with wavelength in the range of 700-900 nm, and is a metal chelate independently selected from:

, and

-continued

In one embodiment, linkers are independently selected from alkane, amino acid, —NHCO(CH$_2$)$_5$—, polyethylene glycol, and polypropylene glycol. In some embodiments, amino acid is natural amino acid. In some embodiments, amino acid is unnatural amino acid. In some embodiments, alkane is C0-C20 straight chain carbon unit. In some embodiments, polyethylene glycol is 1 to 20 ethylene glycol unit. In some embodiments, polypropylene glycol is 1 to 20 propylene glycol unit. In some embodiments, M is independently selected from Cu, Fe, In, Tm, Yb, Y, Gd, Eu, and a lanthanide. In some embodiments, near infrared dye is independently selected from the group of IRDye 800CW, IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 680.

In an another aspect, the present invention provides a method of making a dual-modality probe. The method involves steps of:

(a) Starting synthesis with an organic chelating ligand selected from the group of:

where, R is t-butyl ester, ester, or hydrogen, and
R$^1$ is (b) reacting an organic chelating ligand with a trifunctional linker moiety to result in a trifunctional linker moiety conjugated organic chelating ligand, (c) deprotecting one or more functional group on a trifunctional linker moiety conjugated organic chelating ligand to yield one or more free functional group, (d) chelating a metal ion on one or more free functional group to result in a metal chelate, (e) conjugating a near infrared fluorophore to result in a metal chelated near infrared conjugated carboxylic acid precursor, (f) providing a multivalent scaffold selected from the group of:

where, R$^2$ is Boc, Fmoc, Ac, Cbz, Bz, or Bn,
L$_1$ and L$_2$ are linkers,
and
R$^1$ is (g) conjugating a multivalent scaffold with a targeting ligand to yield one or more targeting ligand conjugated multivalent scaffold, (h) deprotecting an amino protecting group on one or more targeting ligand conjugated multivalent scaffold to obtain an amine containing targeting ligand conjugated multivalent scaffold, and (i) reacting an amine containing targeting ligand conjugated multivalent scaffold with a metal chelated near infrared conjugated carboxylic acid precursor under a condition capable of forming an amide bond to results in a dual-modality probe.

In one embodiment, trifunctional linker moiety is selected from amino acid, polymer, and dendrimer. In some embodiments, linkers are independently selected from alkane, amino acid, —NHCO(CH$_2$)$_5$—, polyethylene glycol, and polypropylene glycol. In some embodiments, amino acid is natural amino acid. In some embodiments, amino acid is unnatural amino acid. In some embodiments, alkane is C0-C20 straight chain carbon unit. In some embodiments, polyethylene glycol is 1 to 20 ethylene glycol unit. In some embodiments, polypropylene glycol is 1 to 20 propylene glycol unit. A targeting ligand is where, $L_3$ is independently selected from the group of alkane, amino acid, polyethylene glycol, and polypropylene glycol. In some embodiments, metal ion is independently selected from Cu, Fe, In, Tm, Yb, Y, Gd, Eu, and a lanthanide. In some embodiments, near infrared fluorophore is independently selected from the group of IRDye 800CW, IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 680.

In an another aspect, the present invention provides a method of making a dual-modality probe. The method involves steps of:

(a) Starting a synthesis with a multivalent scaffold selected from the group of:

where, $R^2$ is Boc, Fmoc, Ac, Cbz, Bz, or Bn,
$L_1$ and $L_2$ are linkers,
and
$R^1$ is (b) conjugating a multivalent scaffold with a targeting ligand to yield one or more targeting ligand conjugated multivalent scaffold, (c) deprotecting an amino protecting group on one or more targeting ligand conjugated multivalent scaffold to obtain an amine containing targeting ligand conjugated multivalent scaffold, (d) reacting an amine containing targeting ligand conjugated multivalent scaffold with a trifunctional linker moiety to result in a trifunctional linker moiety containing targeting ligand conjugated multivalent scaffold, (e) deprotecting one or more functional group on a trifunctional linker moiety containing targeting ligand conjugated multivalent scaffold to yield one or more free functional group, (f) conjugating a near infrared fluorophore to result in a near infrared containing targeting ligand conjugated multivalent scaffold carboxylic acid precursor, (g) providing a metal chelate selected from the group of:

and (h) reacting a metal chelate with a near infrared containing targeting ligand conjugated multivalent scaffold carboxylic acid precursor under a condition capable of forming an amide bond to results in a dual-modality probe.

In one embodiment, trifunctional linker moiety is selected from amino acid, polymer, and dendrimer. In some embodiments, linkers are independently selected from alkane, amino acid, —NHCO(CH$_2$)$_5$—, polyethylene glycol, and polypropylene glycol. In some embodiments, amino acid is natural amino acid. In some embodiments, amino acid is unnatural amino acid. In some embodiments, alkane is C0-C20 straight chain carbon unit. In some embodiments, polyethylene glycol is 1 to 20 ethylene glycol unit. In some embodiments, polypropylene glycol is 1 to 20 propylene glycol unit. A targeting ligand is where, $L_3$ is independently selected from the group of alkane, amino acid, polyethylene glycol, and polypropylene glycol. In some embodiments, metal ion is independently selected from Cu, Fe, In, Tm, Yb, Y, Gd, Eu, and a lanthanide. In some embodiments, near infrared fluorophore is independently selected from the group of IRDye 800CW, IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 680.

The multimeric small-molecule peptidomimetic dual-modality probes generated by present invention can be used for, e.g., optical, magnetic resonance, radioimmuno, PET, and SPECT applications for detection, imaging and treatment of fibrosis and other abnormalities. In particular, multimeric small-molecule peptidomimetic dual-modality probes generated by present invention are specific for integrin $\alpha_v\beta_6$, a fibronectin/tenascin receptor in fibrosis. Specifically, trimerization of an $\alpha_v\beta_6$-selective small-molecule using a rigid admantane core results in significantly higher in vitro affinity for $\alpha_v\beta_6$ in comparison to the monomeric form of an $\alpha_v\beta_6$-selective small-molecule without a rigid admantane core.

With high quantum yields the spectral properties of trimeric dual-modality MRI and optical probe demonstrates peak absorptions (770-780 nm) and emission (790-800 nm), located within the "NIR window," an area of the electromagnetic spectrum that maximizes photon penetration and recovery in living tissue.

The specificities of dual-modality trimer probe 27 (FIG. 7) is evaluated for integrin $\alpha_v\beta_6$-specific cell lines (HT-29 and Huh-7 cells). HT-29 cells express high levels of $\alpha_v\beta_6$-integrin which largely mediates attachment of these cells to fibronectin {Kemperman, 1997}, while Huh-7 cells do not. Dual-modality trimer probe is specific for HT-29 while Huh-7 is negative.

EXAMPLES

1. Preparation of [Gd-DOTA]-Lys-IRDye-CA (FIG. 5)
DOTA(tBu)$_3$-Boc-Lys:
To a solution of N-Boc-L-Lysine (0.06 mmol) in 0.4 mL DMF at 0° C., is added triethylamine (0.12 mmol) followed by dropwise addition of DOTA(tBu)$_3$ NHS ester 16 (0.05 mmol) in 0.5 mL DMF for 10 min with stirring. After 10 min, the ice bath is removed and stirring is continued at room temperature (RT) for 6 h. The reaction mixture is poured over 2 mL ice-cold water and purified by preparative HPLC to obtain DOTA(tBu)$_3$-Boc-Lys 17.

Figure 5:
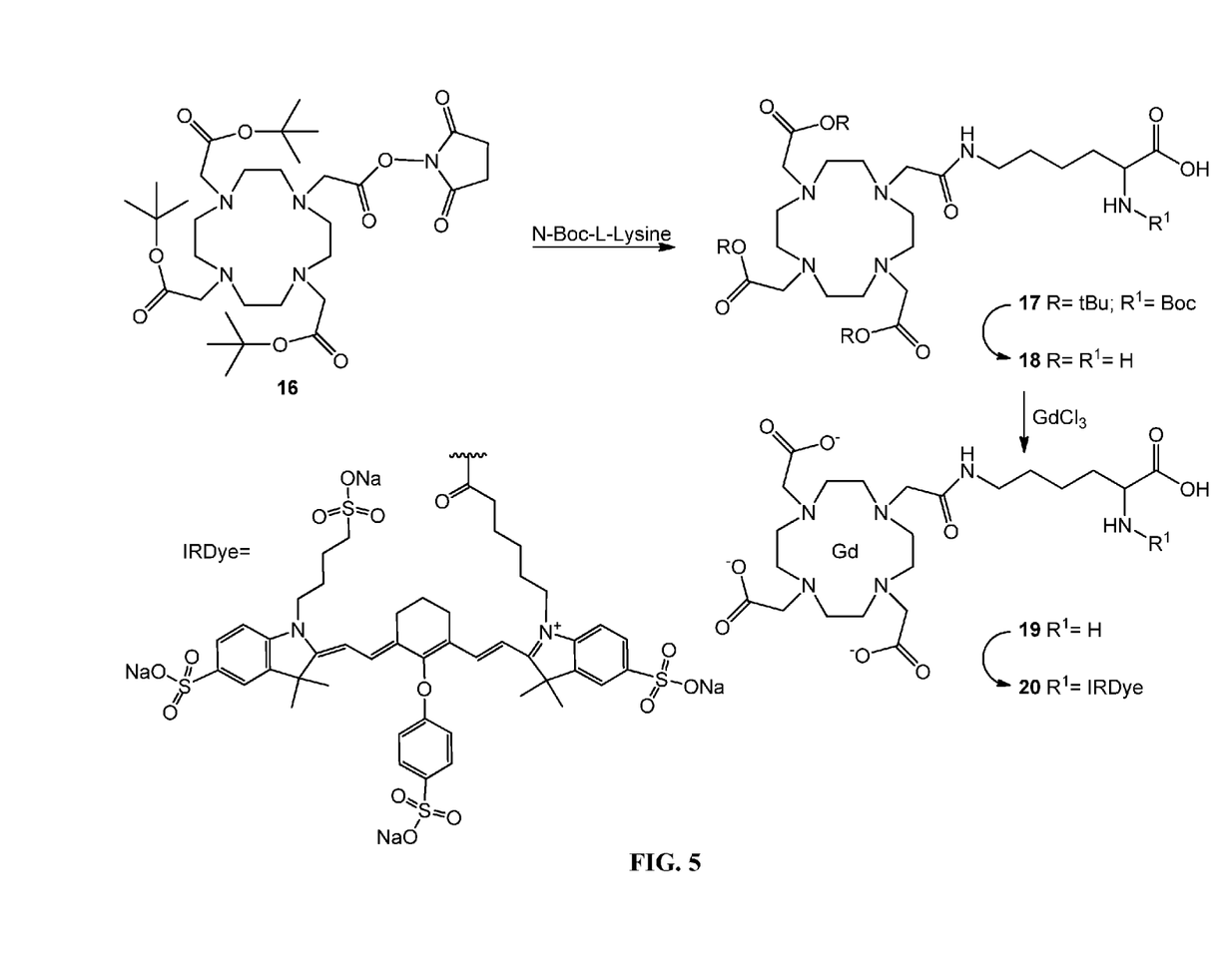
FIG. 5 represents a synthetic scheme for preparation of [Gd-DOTA]-Lys-IRDye-CA.

DOTA-Lys:
DOTA(tBu)$_3$-Boc-Lys 17 (0.045 mmol) is taken in 95% trifluoroacetic acid (TFA, 1 mL). The solution is stirred at RT for 6 h then removed the acid by N$_2$ stream. After lyophilization, DOTA-Lys 18 is obtained without further purification as a white powder.

[Gd-DOTA]-Lys:
The chelation of Gd$^{3+}$ is performed by adding 50 µL of 1 M GdCl$_3$ in water to a solution of DOTA-Lys 18 (0.04 mmol) in 950 µL of 0.5 M HAc/Ac$^-$ buffer, pH 5.5. The reaction mixture is stirred at RT for 12 h. The compound is purified by preparative HPLC to obtain [Gd-DOTA]-Lys 19.

[Gd-DOTA]-Lys-IRDye-CA:
To [Gd-DOTA]-Lys 19 (0.01 mmol) in 1 mL DMSO, is added NHS ester of the NIR fluorophore IRDye 800CW (IRDye-NHS, 0.01 mmol) and N,N-diisopropylethylamine (0.04 mmol) at 0° C. under nitrogen atmosphere. The stirring is continued for 2 h at RT in the dark. The reaction mixture is poured over 4 mL ice-cold water, purified by HPLC and concentrated on an Oasis HLB desalting cartridge as described previously {Bhushan, 2008}. On lyophilization a bright green solid reaction component, [Gd-DOTA]-Lys-IRDye-CA 20 is obtained.

2. Preparation of [Gd-DOTA]-Lys-IRDye-BDP Acid Conjugated Monomer (FIG. 6)
BDP Acid Conjugated Terminal Amine Monomer:
TSTU (0.07 mmol), DIEA (0.08 mmol) and Boc-1,2-diaminoethane (0.068 mmol) are added to BDP acid 21 (0.068 mmol) in 1 mL DMF at 0° C. After 10 min, the ice bath is removed and stirring is continued for 2 h at RT. The reaction mixture is poured over 3 mL ice-cold water and purified by preparative HPLC. After concentration and lyophilization, Boc amine monomer 22 is obtained which is further treated with 1 mL 95% TFA, and the solution is stirred at RT for 2.5 h. The excess TFA is removed by N$_2$ stream. After lyophilization, the BDP acid conjugated terminal amine monomer 23 is obtained without further purification.

Figure 6:
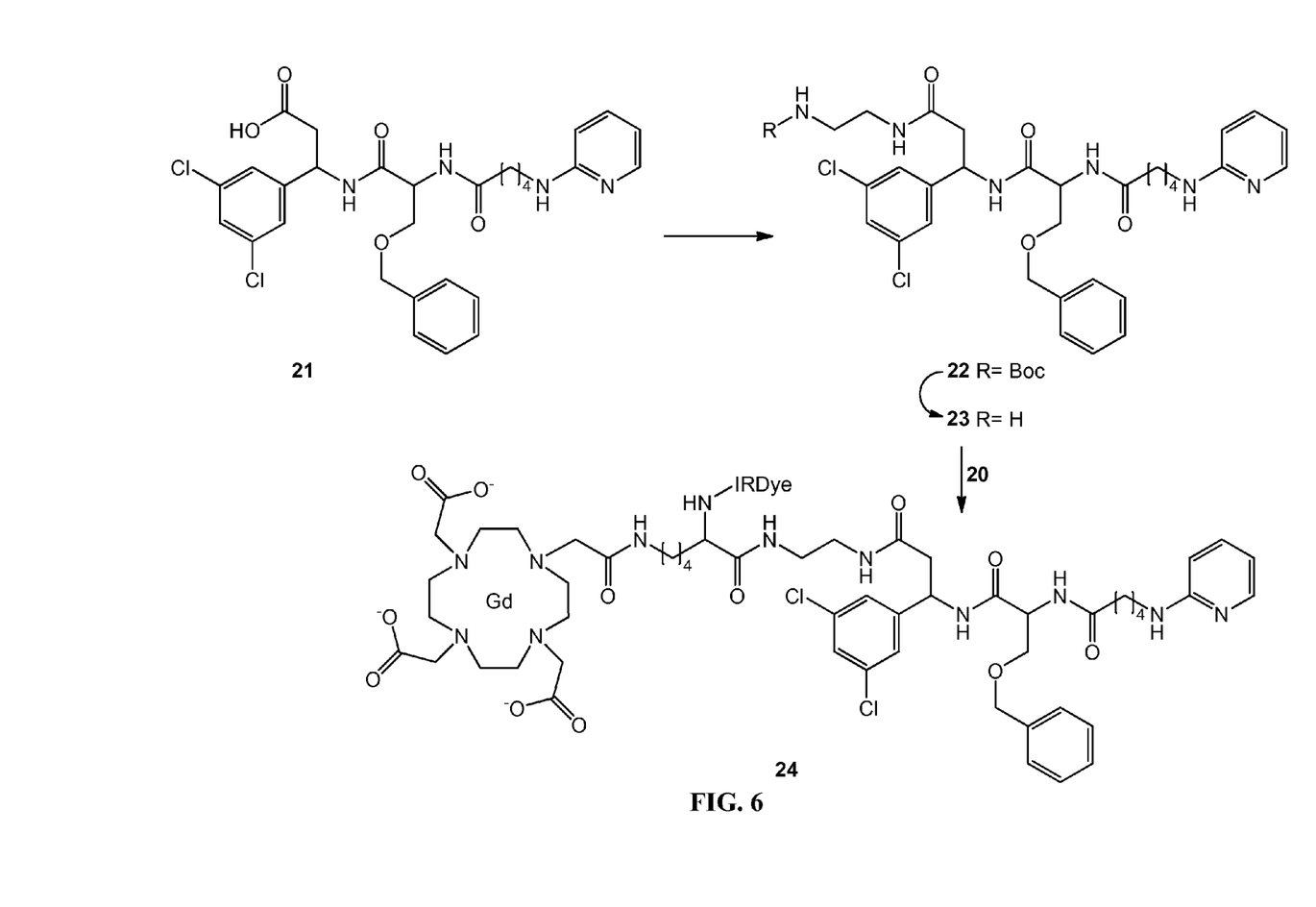
FIG. 6 represents a synthetic scheme for preparation of [Gd-DOTA]-Lys-IRDye-BDP acid conjugated monomer.

[Gd-DOTA]-Lys-IRDye-BDP Acid Conjugated Monomer:
To a solution of [Gd-DOTA]-Lys-IRDye-CA 20 (0.01 mmol) in 1 mL DMSO at 0° C., is added HCTU (0.01 mmol) and NMM (0.05 mmol) followed by dropwise addition of BDP acid conjugated terminal amine monomer 23 (0.01 mmol) in 0.5 mL DMF for 10 min with stirring. After 10 min, the ice bath is removed and stirring is continued at RT for 2 h in the dark. The reaction mixture is poured over 2 mL ice-cold water and purified by preparative HPLC to obtain [Gd-DOTA]-Lys-IRDye-BDP acid conjugated monomer 24.

3. Preparation of [Gd-DOTA]-Lys-IRDye-Ad-BDP Acid Conjugated Trimer (FIG. 7)
Ad-BDP Acid Conjugated Terminal Amine Trimer:
BDP acid conjugated terminal amine monomer 23 (0.06 mmol) is dissolved in 1 mL of DMSO and triethylamine (0.12 mmol). After 5 min, a solution of Boc-NH-Ad-Tri-NHS (0.015 mmol) {Humblet, 2009} in 0.2 mL of DMSO is added. The reaction mixture is stirred at RT for 6 h. The compound 25 is purified after dilution into a final volume of 5 mL with ice-cold water by preparative HPLC system. After lyophilization, product 25 is treated with 95% TFA (1 mL) for 3 h. Excess TFA is removed under nitrogen and after lyophilization the Ad-BDP acid conjugated terminal amine trimer 26 is obtained.

Figure 7:
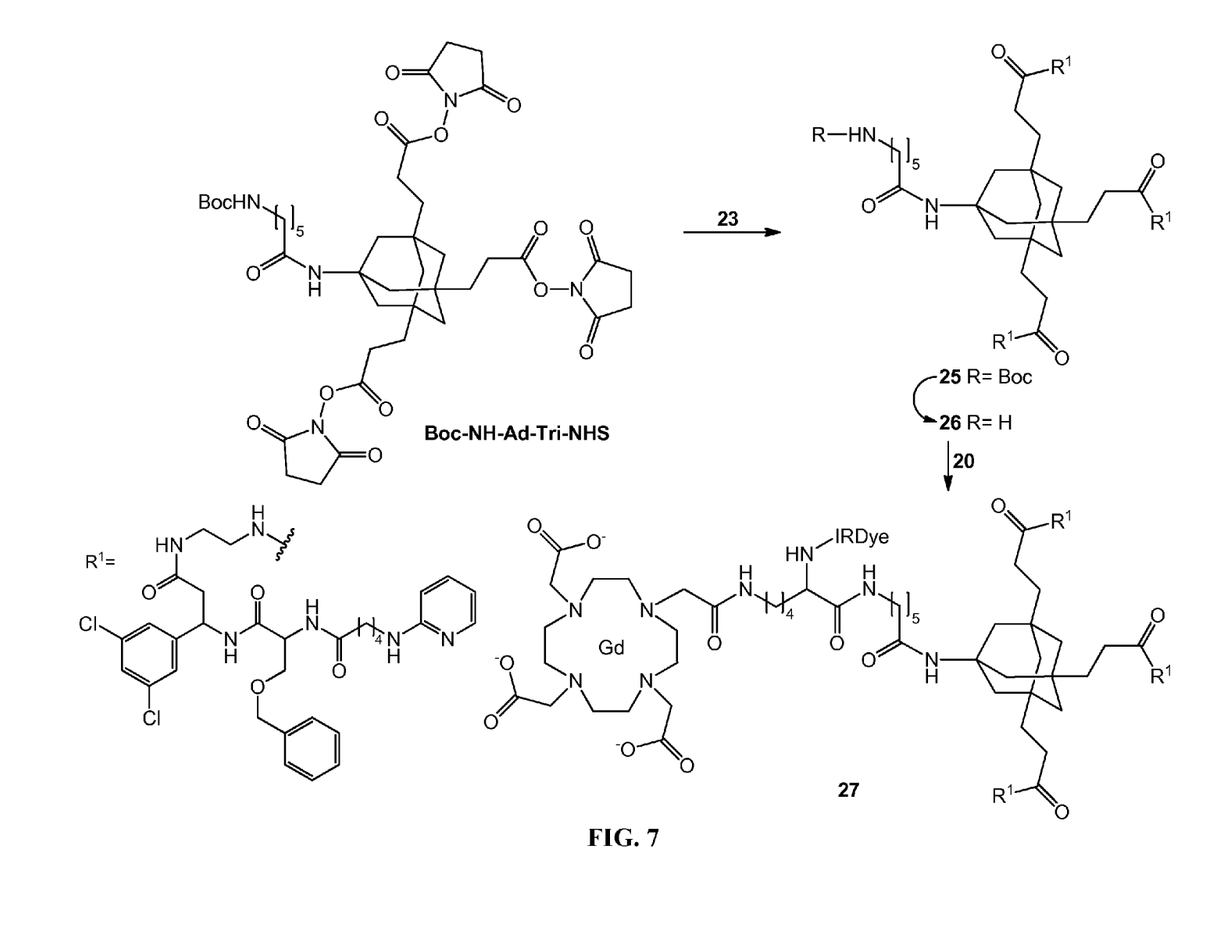
FIG. 7 represents a synthetic scheme for preparation of [Gd-DOTA]-Lys-IRDye-Ad-BDP acid conjugated trimer.

[Gd-DOTA]-Lys-IRDye-Ad-BDP Acid Conjugated Trimer:
To a solution of [Gd-DOTA]-Lys-IRDye-CA 20 (0.01 mmol) in 1 mL DMSO at 0° C., is added HCTU (0.01 mmol) and NMM (0.05 mmol) followed by dropwise addition of Ad-BDP acid conjugated terminal amine trimer 26 (0.01 mmol) in 0.5 mL DMF for 10 min with stirring. After 10 min, the ice bath is removed and stirring is continued at RT for 2 h in the dark. The reaction mixture is poured over 2 mL ice-cold water and purified by preparative HPLC to obtain [Gd-DOTA]-Lys-IRDye-Ad-BDP acid conjugated trimer 27.

4. In Vitro Cell-Binding Assay $\alpha_v\beta_6$-positive human colon carcinoma cell line HT-29 {Kemperman, 1997} and $\alpha_v\beta_6$-negative human hepatoma cell line Huh-7 {Sainz, 2012} are cultured at 37 0° C. under humidified 5% $CO_2$ in RPMI 1640 medium (Mediatech Cellgro, Herndon, Va.) supplemented with 10% fetal bovine serum (Gemini Bio-Products, Woodland, Calif.) and 5% penicillin/streptomycin (Cambrex Bioscience, Walkersville, Md.). For fluorescence study of $\alpha_v\beta_6$-integrin, exponentially growing HT-29 and Huh-7 cells at confluence of 75% on glass coverslips are incubated with 0.2 mL of TBS, PBS, or 100% calf serum containing 2 μM of trimer dual-modality probe for 20 min at RT. The cells are washed three times with TBS, PBS, or serum and fixed with 2% paraformaldehyde in PBS for 10 min at RT. The cells are then permeabilized with PBS supplemented with 0.1% Tween-20. The coverslips are mounted using Fluoromount-G and imaged on NIR fluorescence microscope.

REFERENCES

1. Friedman S L. Hepatic stellate cells: protean, multifunctional, and enigmatic cells of the liver. *Physiol Rev.* 2008, 88, 125-172.

2. Schuppan D, Afdhal N H. Liver cirrhosis. *Lancet* 2008, 371, 838-851.

3. Abraldes J G, Araujo I K, Turon F, Berzigotti, A. Diagnosing and monitoring cirrhosis: liver biopsy, hepatic venous pressure gradient and elastography. *Gastroenterol Hepatol.* 2012, 35, 488-495.

4. Afdhal N H. Biopsy or biomarkers: is there a gold standard for diagnosis of liver fibrosis?. *Clin. Chem.* 2004, 50, 1299-1300.

5. Li H, Gray B D, Corbin I, et. al. MR and fluorescence imaging of low-density lipoprotein receptors. *Acad. Radiol.* 2004, 11, 1251-1259.

6. Bottrill M, Kwok L, Long N J. Lanthanides in magnetic resonance imaging. *Chem. Soc. Rev.* 2006, 35, 557-571.

7. Massoud T F, Gambhir S S. Molecular imaging in living subjects: seeing fundamental biological processes in a new light. *Genes Dev.* 2003, 17, 545-580.

8. Breuss J M, Gallo J, DeLisser H M, et al. Expression of the beta 6 integrin subunit in development, neoplasia and tissue repair suggests a role in epithelial remodeling. *J. Cell Sci.* 1995, 108, 2241-2251.

9. Midwood K S, Mao Y, Hsia H C, Valenick L V, Schwarzbauer J E. Modulation of cell-fibronectin matrix interactions during tissue repair. *J. Investig. Dermatol. Symp. Proc.* 2006, 11, 73-78.

10. Munger J S, Huang X, Kawakatsu H, et al. The integrin alpha v beta 6 binds and activates latent TGF beta 1: a mechanism for regulating pulmonary inflammation and fibrosis. *Cell* 1999, 96, 319-328.

11. Kessler H. Peptide conformations. Part 19. Conformation and biological effects of cyclic peptides. *Angew. Chemie.* 1982, 94, 509-520.

12. Kloczewiak M, Timmons S, Lukas T J, Hawiger J. Platelet receptor recognition site on human fibrinogen. Synthesis and structure-function relationship of peptides corresponding to the carboxy-terminal segment of the gamma chain. *Biochemistry* 1984, 23, 1767-1774.

13. Kraft S, Diefenbach B, Mehta R, Jonczyk A, Luckenbach G A, Goodman S L. Definition of an unexpected ligand recognition motif for alphav beta6 integrin. *J. Biol. Chem.* 1999, 274, 1979-1985.

14. Kitov P I, Bundle D R. On the nature of the multivalency effect: a thermodynamic model. *J. Am. Chem. Soc.* 2003, 125, 16271-16284.

15. Mammen M, Chio S K, Whitesides G M. Polyvalent interactions in biological systems: implications for design and use of multivalent ligands and inhibitors. *Angew. Chem., Int. Ed.* 1998, 37, 2755-2794.

16. Lindhorst T K. Artificial multivalent sugar ligands to understand and manipulate carbohydrate-protein interactions. *Top. Curr. Chem.* 2002, 218, 201-235.

17. Lundquist J J, Toone E J. The cluster glycoside effect. *Chem. Rev.* 2002, 102, 555-578.

18. Wright D, Usher L. Multivalent binding in the design of bioactive compounds. *Curr. Org. Chem.* 2001, 5, 1107-1131.

19. Carlson C, Mowery P, Owen R, Dykhuizen E, Kiessling, L. Selective tumor cell targeting using low-affinity, multivalent interactions. *ACS Chem. Biol.* 2007, 2, 119-127.

20. Thumshirn G, Hersel U, Goodman S L, Kessler H. Multimeric cyclic RGD peptides as potential tools for tumor targeting: solid-phase peptide synthesis and chemoselective oxime ligation. *Chem. Eur. J.* 2003, 9, 2717-2725.

21. Voegtle F, Richardt G, Werner N. *Dendritische Moleküle*; B. G. Teubner Verlag: Wiesbaden, Germany, 2007.

22. Haag R, Kratz F. Polymer therapeutics: concepts and applications. *Angew. Chem. Int. Ed.* 2006, 45, 1198-1215.

23. Popov Y, Patsenker E, Stickel F, et. al. Integrin alphavbeta6 is a marker of the progression of biliary and portal liver fibrosis and a novel target for antifibrotic therapies. *J. Hepatol.* 2008, 48, 453-464.

24. Kemperman H, Wijnands Y M, Roos E. alphaV Integrins on HT-29 colon carcinoma cells: adhesion to fibronectin is mediated solely by small amounts of alphaVbeta6, and alphaVbeta5 is codistributed with actin fibers. *Exp Cell Res.* 1997, 234, 156-164.

25. Bhushan K R, Misra P, Liu F, et. al. Detection of breast cancer microcalcifications using a dual-modality SPECT/NIR fluorescent probe. *J. Am. Chem. Soc.* 2008, 130, 17648-17649.

26. Humblet V, Misra P, Bhushan K R, et al. Multivalent scaffolds for affinity maturation of small molecule cell surface binders and their application to prostate tumor targeting. *J. Med. Chem.* 2009, 52, 544-550.

27. Sainz B, Barretto N, Yu X, Corcoran P, Uprichard S L. Permissiveness of human hepatoma cell lines for HCV infection. *Virology J.* 2012, 9, 30-39.

What is claimed is:

1. A dual-modality probe having a formula selected from the group consisting of:

-continued wherein is

R is

$L_1$, $L_2$, $L_3$, $L_4$, $L_5$ and $L_6$ are linkers;

IRDye is a near infrared dye with wavelength in the range of 700-900 nm;

and is a metal chelate independently selected from:

, and

-continued

2. The dual-modality probe of claim 1, wherein said linkers are selected from the group consisting of alkane, amino acid, —NHCO(CH$_2$)$_5$—, polyethylene glycol, and polypropylene glycol.

3. The dual-modality probe of claim 1, wherein said dual-modality probe is in a form of pharmaceutically acceptable salts, hydrates, and solvates.

4. The dual-modality probe of claim 1, wherein M is selected from the group consisting of Cu, Fe, In, Mn, Tm, Yb, Y, Gd, Eu, and a lanthanide.

5. The dual-modality probe of claim 1, wherein said near infrared dye is selected from the group consisting of IRDye 800CW, IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 680.

6. The dual-modality probe of claim 1, wherein said metal chelate and said IRDye are conjugated for concurrent magnetic resonance and near infrared optical imaging.

7. A method of making a dual-modality probe, said method comprising:
(a) providing an organic chelating ligand, wherein said organic chelating ligand selected from the group consisting of:

wherein
R is t-butyl ester, ester, or hydrogen;

and
R$^1$ is (b) reacting said organic chelating ligand with a trifunctional linker moiety to result in a trifunctional linker moiety conjugated organic chelating ligand;
(c) deprotecting one or more functional group on said trifunctional linker moiety conjugated organic chelating ligand to yield one or more free functional group;
(d) chelating a metal ion on said one or more free functional group to result in a metal chelate;
(e) conjugating a near infrared fluorophore to result in a metal chelated near infrared conjugated carboxylic acid precursor;
(f) providing a multivalent scaffold, wherein said multivalent scaffold is selected from the group consisting of:

wherein
R$^2$ is Boc, Fmoc, Ac, Cbz, Bz, or Bn;
L$_1$ and L$_2$ are linkers;
and
R$^1$ is (g) conjugating said multivalent scaffold with a targeting ligand to yield one or more targeting ligand conjugated multivalent scaffold; wherein said targeting ligand is

19 wherein $L_3$ is independently selected from the group consisting of alkane, amino acid, polyethylene glycol, and polypropylene glycol (h) deprotecting an amino protecting group on said one or more targeting ligand conjugated multivalent scaffold to obtain an amine containing targeting ligand conjugated multivalent scaffold; and (i) reacting said amine containing targeting ligand conjugated multivalent scaffold with said metal chelated near infrared conjugated carboxylic acid precursor under a condition capable of forming an amide bond to results in said dual-modality probe.

8. The method of claim 7, wherein said linkers are selected from the group consisting of alkane, amino acid, —NHCO(CH$_2$)$_5$—, polyethylene glycol, and polypropylene glycol.

9. The method of claim 7, wherein said dual-modality probe is in a form of pharmaceutically acceptable salts, hydrates, and solvates.

10. The method of claim 7, wherein said metal ion is selected from the group consisting of Cu, Fe, In, Mn, Tm, Yb, Y, Gd, Eu, and a lanthanide.

11. The method of claim 7, wherein said near infrared fluorophore is selected from the group consisting of IRDye 800CW, IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 680.

12. The method of claim 7, wherein said trifunctional linker moiety is amino acid, polymer, or dendrimer.

13. A method of making a dual-modality probe, said method comprising:

(a) providing a multivalent scaffold, wherein said multivalent scaffold is selected from the group consisting of:

and

20

-continued wherein $R^2$ is Boc, Fmoc, Ac, Cbz, Bz, or Bn;

$L_1$ and $L_a$ are linkers;

and $R_1$ is (b) conjugating said multivalent scaffold with a targeting ligand to yield one or more targeting ligand conjugated multivalent scaffold; wherein said targeting ligand is wherein $L_3$ is independently selected from the group consisting of alkane, amino acid, polyethylene glycol, and polypropylene glycol

(c) deprotecting an amino protecting group on said one or more targeting ligand conjugated multivalent scaffold to obtain an amine containing targeting ligand conjugated multivalent scaffold;

(d) reacting said amine containing targeting ligand conjugated multivalent scaffold with a trifunctional linker moiety to result in a trifunctional linker moiety containing targeting ligand conjugated multivalent scaffold;

(e) deprotecting one or more functional group on said trifunctional linker moiety containing targeting ligand conjugated multivalent scaffold to yield one or more free functional group;

(f) conjugating a near infrared fluorophore to result in a near infrared containing targeting ligand conjugated multivalent scaffold carboxylic acid precursor;

(g) providing a metal chelate, wherein said metal chelate selected from the group consisting of:

and (h) reacting said metal chelate with said near infrared containing targeting ligand conjugated multivalent scaffold carboxylic acid precursor under a condition capable of forming an amide bond to results in said dual-modality probe.

14. The method of claim 13, wherein said linkers are selected from the group consisting of alkane, amino acid, —NHCO(CH$_2$)$_5$—, polyethylene glycol, and polypropylene glycol.

15. The method of claim 13, wherein said dual-modality probe is in a form of pharmaceutically acceptable salts, hydrates, and solvates.

16. The method of claim 13, wherein said near infrared fluorophore is selected from the group consisting of IRDye 800CW, IRDye 78, IRDye 700DX, VivoTag-S 750, VivoTag 800, VivoTag-S 680, DY-750, DY-682, DY-675, Cypate, Cy7, Alexa Fluor 750, and Alexa Fluor 680.

17. The method of claim 13, wherein M is selected from the group consisting of Cu, Fe, In, Mn, Tm, Yb, Y, Gd, Eu, or a lanthanide.

18. The method of claim 13, wherein said trifunctional linker moiety is amino acid, polymer, or dendrimer.

* * * * *